(12) United States Patent
Murakami et al.

(10) Patent No.: US 10,836,723 B2
(45) Date of Patent: Nov. 17, 2020

(54) METHOD FOR SYNTHESIZING SODIUM 2,2,6,6-TETRAMETHYLPIPERIDIDES

(71) Applicant: KOBELCO ECO-SOLUTIONS CO., LTD., Hyogo (JP)

(72) Inventors: Yoshiaki Murakami, Hyogo (JP); Miyuki Fukushima, Hyogo (JP); Kazuhiko Takai, Okayama (JP); Sobi Asako, Okayama (JP)

(73) Assignee: KOBELCO ECO-SOLUTIONS CO., LTD., Hyogo (JP)

( * ) Notice: Subject to any disclaimer, the term of this patent is extended or adjusted under 35 U.S.C. 154(b) by 0 days.

(21) Appl. No.: 16/480,761

(22) PCT Filed: Jan. 24, 2018

(86) PCT No.: PCT/JP2018/002054
§ 371 (c)(1),
(2) Date: Jul. 25, 2019

(87) PCT Pub. No.: WO2018/139470
PCT Pub. Date: Aug. 2, 2018

(65) Prior Publication Data
US 2019/0359571 A1    Nov. 28, 2019

(30) Foreign Application Priority Data

Jan. 27, 2017 (JP) .................. 2017-012636
Nov. 8, 2017 (JP) .................. 2017-215392

(51) Int. Cl.
*C07D 211/92* (2006.01)
*C07F 1/04* (2006.01)

(52) U.S. Cl.
CPC .............. *C07D 211/92* (2013.01); *C07F 1/04* (2013.01)

(58) Field of Classification Search
CPC ............................ C07D 211/12; C07D 211/92
USPC ...................................................... 546/184
See application file for complete search history.

(56) References Cited

U.S. PATENT DOCUMENTS

| 2,914,578 | A | 11/1959 | Nobis et al. |
| 10,294,193 | B2 * | 5/2019 | Adachi ............... A61K 8/33 |
| 2017/0088503 | A1 | 3/2017 | Adachi et al. |

FOREIGN PATENT DOCUMENTS

| JP | 49-217 A | 1/1974 |
| WO | 93/14061 A1 | 7/1993 |
| WO | 2015/186614 A1 | 12/2015 |

OTHER PUBLICATIONS

Maruzen Inc., Feb. 28, 2003; pp. 164-165 (Matsubayashi, Genetsu, Complex and organometallic chemistry).
Armstrong et al., "A Structural and Computational Study of Synthetically Important Alkali-Metal/Tetramethylpiperidide (TMP) Amine Solvates," Chem. Eur. J. 2008, 14(26): pp. 8025-8084.
Kodera et al., "Synthesis of Sodium 2,2,6,6-Tetramethylpiperidide Using Sodium Dispersion, and Its Synthetic Application," The Chemical Society of Japan Spring Annual Meeting, Mar. 3, 2017, vol. 97, p. 2E2-08.
Kodera et al., "Synthesis using sodium dispersion of NaTMP, and application to reaction," Lecture Abstracts of Organic Synthesis Symposium, Jun. 8, 2017, vol. 111: p. 143.
Gehrhus et al., "Synthesis and crystal structure of trimeric sodium 2,2,6,6-tetramethylpiperidide (NaTMP)," Journal of Organometallic Chemistry 587 (1999), pp. 88-92.
Office Actions dated Mar. 30, 2018 and Jun. 11, 2018 in priority Japanese appln. No. 2017-215392 and English translations thereof.
Translation of the International Preliminary Report on Patentability from PCT/JP2018/002054 and Notification of Transmittal dated Aug. 8, 2019.

* cited by examiner

*Primary Examiner* — Patricia L Morris
(74) *Attorney, Agent, or Firm* — Dilworth & Barrase, LLP

(57) ABSTRACT

There is a demand for the development of a technique according to which sodium 2,2,6,6-tetramethylpiperidides (Na-TMPs) can be economically and efficiently synthesized through simple operations including a small number of steps under mild conditions in a short period of time. Also, there is a demand for the development of a technique according to which high-quality Na-TMPs that do not contain lithium or lithium compounds such as Li-TMP can be synthesized. The method for synthesizing sodium 2,2,6,6-tetramethylpiperidides includes a step of obtaining sodium 2,2,6,6-tetramethylpiperidides by reacting, in a reaction solvent, 2,2,6,6-tetramethylpiperidines with a dispersion product obtained by dispersing sodium in a dispersion solvent or an organosodium compound having an aromatic ring obtained through a reaction with a dispersion product obtained by dispersing sodium in a dispersion solvent.

3 Claims, 5 Drawing Sheets

| Experiment Number | X | Y | Yield/%[a] | Ph–Ph/%[a] |
|---|---|---|---|---|
| 1 | Br | 2.0 | 90 | 3 |
| 2 | Br | 2.1 | 94 | 1 |
| 3 | Br | 2.2 | >99 | trace |
| 4 | Br | 2.3 | >99 | trace |
| 5 | Cl | 1.95 | 81 | 15 |
| 6 | Cl | 2.0 | 92 | trace |
| 7 | Cl | 2.1 | >99 | trace |
| 8 | Cl | 2.2 | >99 | trace |
| 9 | Cl | 2.3 | >99 | trace |

[a] Measurement by $^1$H NMR

| Experiment Number | Period of time / hours | Yield of Na–TMP / % |
|---|---|---|
| 1 | 0.5 | 79 |
| 2 | 1 | 88 |
| 3 | 3 | 87 |
| 4 | 6 | 86 |
| 5 | 12 | 89 |
| 6 | 24 | 80 |

| Experiment Number | Temperature °C | Period of time hours | Yield of Na-TMP % |
| --- | --- | --- | --- |
| 1 | 0 | 0 | 98 |
| 2 | 0 | 1 | 91 |
| 3 | 0 | 3 | 75 |
| 4 | 0 | 6 | 63 |
| 5 | 0 | 12 | 63 |
| 6 | 0 | 18 | 44 |
| 7 | 0 | 24 | 38 |
| 8 | −20 | 0 | 98 |
| 9 | −20 | 1 | 89 |
| 10 | −20 | 3 | 90 |
| 11 | −20 | 6 | 84 |
| 12 | −20 | 12 | 73 |
| 13 | −20 | 18 | 56 |
| 14 | −20 | 24 | 51 |

| Experiment Number | Period of time hours | Yield of Na-TMP % | Age in days of SD days |
| --- | --- | --- | --- |
| 1 | 0.5 | 90 | 4 |
| 2 | 1 | 89 | 6 |
| 3 | 1 | 88 | 8 |
| 4 | 1 | 87 | 10 |
| 5 | 1 | 82 | 13 |
| 6 | 1 | 77 | 30 |
| 7 | 1 | 72 | 32 |

| Experiment Number | Base | Yield/% | E/Z |
|---|---|---|---|
| 1 | LiTMP(1.25molar equivalents) | 89 | 18/82 |
| 2 | LiTMP/$^t$BuONa(1.4molar equivalents) | 96 | 12/88 |
| 3 | NaTMP(1.25molar equivalents) | 92 | 8/92 |

| Experiment Number | Base | Reaction solvent | Temperature | Yield/% 1 | 2 E/Z |
|---|---|---|---|---|---|
| 1 | NaTMP | Hexane | 0 | 1 | 98(73/27) |
| 2 | NaTMP | THF:Hexane=1:2 | 0 | 3 | 90(78/22) |
| 3 | NaTMP | Hexane | 25 | 2 | 91(62/38) |
| 4 | NaTMP(10 mol %)[a] | Hexane | 25 | 1 | 98(73/27) |
| 5 | LiTMP | THF | 25 | 95 | 4(45/55) |
| 6 | LiTMP | THF | 50 | 59 | 39(47/53) |

[a] 5 hours

Fig.9

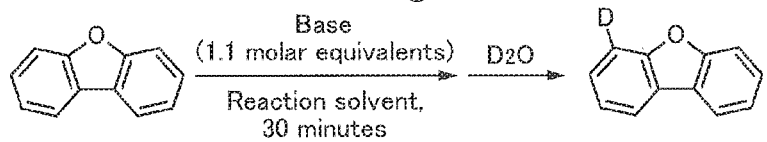

| Experiment Number | Base | Reaction solvent | Temperature | D ratio/% |
|---|---|---|---|---|
| 1 | $^n$BuLi | Hexane | 25 | 79 |
| 2 | $^n$BuLi | THF/Hexane (1/2) | 0 | 85 |
| 3 | LiTMP | Hexane | 25 | 14 |
| 4 | LiTMP | THF/Hexane (1/2) | 0 | 50 |
| 5 | NaTMP | Hexane | 25 | 90 |

Fig.10

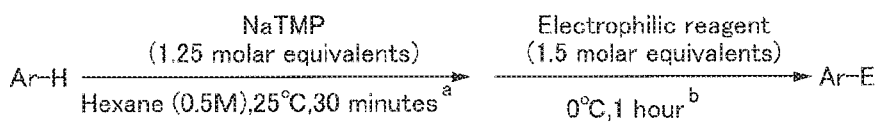

| Experiment Number | Arene | Electrophilic reagent | Product | Isolated yield % |
|---|---|---|---|---|
| 1 | benzothiophene | $B(OMe)_3$ | 2-E benzothiophene | 64(E=B(OH)$_2$)$^a$ |
| 2 | | $D_2O$ | | 99(E=D) |
| 3 | | MeI | | 77(E=Me) |
| 4 | | Allyl Br | | 82(E=Allyl) |
| 5 | | PhC(O)Cl | | 66(E=Benzoyl) |
| 6 | | $CO_2$ | | 89(E=$CO_2$H) |
| 7 | | $Br_2HCCHBr_2$ | | 81(E=Br)$^b$ |
| 8 | | $Cl_3CCCl_3$ | | 91(E=Cl)$^b$ |
| 9 | | $Me_3SiCl$ | | 98(E=SiMe$_3$) |
| 10 | | $Ph_2PCl$ | | 72(E=PPh$_2$) |
| 11 | benzofuran | $Me_3SiCl$ | 2-E benzofuran | 82(E=SiMe$_3$) |
| 12 | dibenzofuran | $Me_3SiCl$ | 4-E dibenzofuran | 83(E=SiMe$_3$) |
| 13 | | PhC(O)Cl | | 73(E=Benzoyl) |

$^a$ Room temperature, 1 hour  $^b$ −78°C, 1 hour

METHOD FOR SYNTHESIZING SODIUM 2,2,6,6-TETRAMETHYLPIPERIDIDES

TECHNICAL FIELD

The present invention relates to a method for synthesizing sodium 2,2,6,6-tetramethylpiperidides.

BACKGROUND ART

Metal amide compounds are organic bases having a metal-nitrogen bond in their molecules, and are widely used in agrochemical and pharmaceutical organic synthesis chemistry. Compounds obtained by substituting a hydrogen atom in a secondary amine by a metal atom such as an alkali metal are suitably used, and examples thereof include lithium 2,2,6,6-tetramethylpiperidide (which may be abbreviated as "Li-TMP" hereinafter) and sodium 2,2,6,6-tetramethylpiperidide (which may be abbreviated as "Na-TMP" hereinafter) having a tetrasubstituted carbon atom at α-position.

Conventionally, it is reported that, as a method for manufacturing Na-TMP, by reacting, in a pentane solvent (50 ml), 2,2,6,6-tetramethylpiperidine (44 mmol) (which may be abbreviated as "TMP" hereinafter) with 0.95 equivalents of n-butyl sodium (42 mmol) (which may be abbreviated as "$^n$BuNa" hereinafter), Na-TMP was obtained at a yield of 82% at an outside air temperature (25° C.) (Non-Patent Document 1).

It is also reported in Non-Patent Document 1 that Na-TMP was obtained at a yield of 87% through a reaction, in a hexane solvent (50 ml), between Li-TMP (38 mmol) and 1 equivalent of sodium t-butoxide (38 mmol) (which may be abbreviated as "NaO$^t$Bu" hereinafter) at an outside air temperature (25° C.).

CITATION LIST

Non-Patent Documents

Non-Patent Document 1: B. Gehrhus et al., "Synthesis and crystal structure of trimericsodium 2,2,6,6-tetramethylpiperidide (NaTMP)", Journal of Organometallic Chemistry, 587(1), 1999, p 88-92

SUMMARY OF INVENTION

Technical Problem

However, in the method disclosed in Non-Patent Document 1 in which TMP and $^n$BuNa are used, $^n$BuNa is prepared through a metathesis reaction between n-butyllithium (referred to as "$^n$BuLi" hereinafter) and NaO$^t$Bu, and thus the obtained $^n$BuNa contains lithium and lithium compounds. Thus, there is a problem in that Na-TMP obtained as a result contains lithium and lithium compounds such as Li-TMP as impurities. Also, there is a problem in that a synthesis process includes multiple steps due to including a $^n$BuNa preparation process, and the production cost is increased due to an expensive agent such as $^n$BuLi being used in preparation of $^n$BuNa, for example. Furthermore, $^n$BuLi is designated as Category III hazardous materials in the Fire Service Act, and thus an apparatus suitable for handling and the like are required.

The method disclosed in Non-Patent Document 1 in which Li-TMP and NaO$^t$Bu are used is for synthesizing Na-TMP in a single step. However, Li-TMP needs to be obtained through a reaction between $^n$BuLi and TMP, resulting in a reaction substantially including multiple steps. Also, because Li-TMP is used, similarly to the above-described method, lithium and lithium compounds such as Li-TMP are mixed therein as impurities, and thus it is difficult to obtain high-quality Na-TMP. Thus, there is a problem in that a synthetic reaction system in which Na-TMP is used alone as an organic base cannot be developed because an unfavorable side-reaction occurs due to a difference in the reactivity between Na-TMP and Li-TMP, for example.

In view of this, there is a demand for the development of a technique according to which Na-TMPs can be economically and efficiently synthesized through simple operations including a small number of steps under mild conditions in a short period of time. Also, there is a demand for the development of a technique according to which high-quality Na-TMPs that do not contain lithium or lithium compounds such as Li-TMP can be synthesized.

Solution to Problem

As a result of performing intensive studies to solve the foregoing problems, the inventors of the present invention found that Na-TMPs can be stably and efficiently synthesized by reacting TMPs with a dispersion product obtained by dispersing sodium in a dispersion solvent or an organosodium compound having an aromatic ring obtained through a reaction with a dispersion product obtained by dispersing sodium in a dispersion solvent. Such a method for synthesizing Na-TMPs does not require expensive agents, expensive apparatuses, or the like, and is thus economically advantageous, and Na-TMPs can be synthesized using this method through a small number of steps in a simple manner in a short period of time without requiring a complicated chemical technique. Also, high-quality Na-TMPs can be obtained because a lithium compound that is required in a conventional method is not used in a synthesis process. The inventors of the present invention achieved the present invention based on these findings.

That is, the present invention relates to a method for synthesizing sodium 2,2,6,6-tetramethylpiperidides (Na-TMPs), and a characteristic configuration thereof includes a step of obtaining sodium 2,2,6,6-tetramethylpiperidides (Na-TMPs) by reacting, in a reaction solvent, 2,2,6,6-tetramethylpiperidines (TMPs) with a dispersion product (SD) obtained by dispersing sodium in a dispersion solvent or an organosodium compound having an aromatic ring obtained through a reaction with a dispersion product (SD) obtained by dispersing sodium in a dispersion solvent.

According to this configuration, as a result of adding SD or an organosodium compound using TMPs as starting materials, Na-TMPs can be stably and efficiently synthesized. In this configuration, Na-TMP can be stably synthesized in a uniform temperature distribution due to SD used in the method for synthesizing Na-TMPs uniformly dispersing throughout the reaction system. Also, according to this configuration, SD, which is easy to handle, is used, and thus Na-TMPs can be manufactured through a small number of steps under mild conditions in a simple manner in a short period of time without requiring a complicated chemical technique, and this configuration is economically and industrially very advantageous. Also, because TMPs are bulky and electron-rich, anions formed due to protons of nitrogen of TMPs being removed are unstable. Thus, it is difficult to produce sodium amide of TMPs, but according to this configuration, as a result of using SD, this synthetic reaction system can stably proceed, and Na-TMPs can be stably and efficiently synthesized.

In another characteristic configuration, the above-described step is carried out in the presence of amines.

According to this configuration, as a result of adding amines, a reaction system for synthesizing Na-TMPs is stabilized and the progress of the reaction can be facilitated, and Na-TMPs can be more stably and efficiently synthesized. The obtained effects are that stabilization of the synthetic reaction system increases the frequency of collision between TMPs and SD or an organosodium compound, stabilization of reaction energy and the like increases the force for driving the reaction system for synthesizing Na-TMPs, and the progress of the synthetic reaction is facilitated and the yield is increased. Also, as described above, because TMPs are bulky and electron-rich, anions formed due to protons of nitrogen of TMPs being removed are unstable. Thus, it is difficult to produce sodium amides of TMPs, but, as with this configuration, as a result of using amines in addition to SD, this synthetic reaction system can stably proceed and Na-TMPs can be stably and efficiently synthesized.

BRIEF DESCRIPTION OF DRAWINGS

FIG. 9 is a diagram summarizing the investigation conditions and the investigation results of Example 7 in which reactions (deprotonation and a functionalization reaction of a heteroarene) in which Na-TMP synthesized using a method for synthesizing Na-TMPs according to this embodiment was used were investigated.

FIG. 10 is a diagram summarizing the investigation conditions and the investigation results of Example 8 in which reactions (functionalization of a heterocyclic compound) in which Na-TMP synthesized using a method for synthesizing Na-TMPs according to this embodiment is used were investigated.

Figure 1:
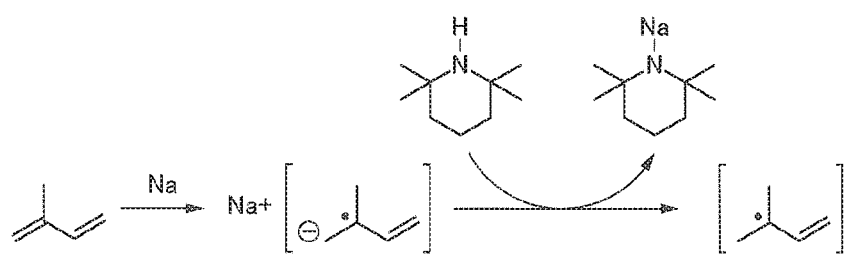
FIG. 1 is a diagram illustrating a mechanism of a reaction of a method for synthesizing Na-TMPs according to this embodiment.

DESCRIPTION OF EMBODIMENTS (Method for Synthesizing Na-TMPs According to Embodiment of Present Invention)

Hereinafter, an embodiment of a method for synthesizing Na-TMPs according to the present invention will be described in detail. Note that the present invention is not limited to embodiments, which will be described later.

The method for synthesizing Na-TMPs according to this embodiment includes a step of obtaining Na-TMPs by reacting, in a reaction solvent, TMPs with a dispersion product obtained by dispersing sodium in a dispersion solvent or an organosodium compound having an aromatic ring obtained through a reaction with a dispersion product obtained by dispersing sodium in a dispersion solvent.

Here, an example of Na-TMPs is sodium 2,2,6,6-tetramethylpiperidide (Na-TMP) that may or may not have a substituent. In a case where a substituent is present, for example, a substituent may be substituted for a portion or all of carbon atoms located at 3-, 4-, and 5-positions of a piperidine ring, and in a case where a plurality of substituents are present, portions or all of them may be the same or all of them are different from each other. Although examples of the substituent include alkyl groups such as a methyl group, an ethyl group, and a propyl group, the substituent is not limited thereto.

TMPs, which are starting materials in the method for synthesizing Na-TMPs according to this embodiment, are 2,2,6,6-tetramethylpiperidines that may or may not have a substituent, and are set as appropriate according to desired Na-TMPs. Thus, in a case where a substituent is present, for example, a substituent may be substituted according to desired Na-TMPs, for a portion or all of carbon atoms located at 3-, 4-, and 5-positions of a piperidine ring, and in a case where a plurality of substituents are present, portions or all of them may be the same or all of them may be different from each other. Although examples of the substituent include alkyl groups such as a methyl group, an ethyl group, and a propyl group, the substituent is not limited thereto.

TMPs can be synthesized using a method known in the art, and for example, TMP can be obtained from 2,2,6,6-tetramethyl-4-piperidone (triacetoneamine) obtained through a 1,4-addition reaction or the like of ammonia to 2,6-dimethyl-2,5-heptadien-4-one (holon), through reduction with tin, zinc, and sodium amalgam, or catalytic hydrogenation etc.

Although TMP can also be obtained through Wolff-Kishner reduction of triacetoneamine, the method is not limited thereto. Also, commercially available TMPs can be suitably used.

The dispersion product obtained by dispersing sodium in a dispersion solvent in the method for synthesizing Na-TMPs according to this embodiment is a dispersion product obtained by dispersing minute particles of sodium in an insoluble solvent, or a dispersion product obtained by dispersing sodium in a liquid form in an insoluble solvent. The average particle diameter of the minute particles is preferably less than 10 μm, and the minute particles having an average particle diameter of less than 5 μm can be used particularly preferably. The diameter of a sphere having a projected area equal to the projected area obtained through image analyses of photomicrographs is taken as the average particle diameter.

A solvent known in the art can be used as the dispersion solvent as long as minute particles of sodium or sodium in a liquid form can be dispersed in an insoluble solvent, and the reaction of TMPs with sodium included in the dispersion product obtained by dispersing sodium in a dispersion solvent is not inhibited. Examples thereof include aromatic solvents such as xylene and toluene, normal paraffin-based solvents such as decane, heterocyclic compound-based solvents such as tetrahydrothiophene, and mixed solvents thereof.

Hereinafter, the dispersion product obtained by dispersing an alkali metal in a dispersion solvent may be abbreviated as "SD". SD is an abbreviation of "sodium dispersion".

A solvent known in the art can be used as the reaction solvent used in the method for synthesizing Na-TMPs according to this embodiment as long as the reaction of TMPs with SD is not inhibited. Examples thereof include ether-based solvents, normal paraffin-based solvents, cycloparaffin-based solvents, aromatic solvents, amine-based solvents, and heterocyclic compound-based solvents. As the ether-based solvent, a cyclic ether-based solvent is preferable, and tetrahydrofuran is particularly preferable. As the normal paraffin-based solvent and the cycloparaffin-based solvent, hexane, normal decane, cyclohexane, or the like is particularly preferable. As the aromatic solvent, xylene, toluene, benzene, or the like is preferable. As the amine-based solvent, ethylenediamine or the like is preferable. Also, as the heterocyclic compound-based solvent, tetrahydrothiophene or the like can be preferably used. These solvents may be used alone or in combination of two or more as a mixed solvent. Here, the above-described dispersion solvent and the reaction solvent may be the same or different.

In the method for synthesizing Na-TMPs according to this embodiment, an organosodium compound having an aromatic ring obtained through a reaction with SD can be used, instead of SD. The organosodium compound having an aromatic ring may be a compound having one or more aromatic rings and one or more carbon atom-sodium bonds in its molecule, and preferably, a compound in which a carbon atom of an aromatic ring is linked to sodium. The aromatic ring refers to a hydrocarbon aromatic ring constituted by only a hydrocarbon and heteroaromatic ring including an atom other than a carbon atom in its ring structure, and preferably a hydrocarbon aromatic ring. Also, the aromatic ring may be a single ring or a collective ring, a fused polycyclic ring, or the like having multiple rings. Although examples of the aromatic ring include a benzene ring, a naphthalene ring, an anthracene ring, a pyridine ring, and an imidazole ring, the aromatic ring is not limited thereto. Although the aromatic ring may have one or more substituents or no substituents, and examples of the substituent include alkyl groups such as a methyl group, an ethyl group, and a propyl group, the substituent is not limited thereto.

Although specific examples of the organosodium compound having an aromatic ring (which may be abbreviated as "organosodium compound" hereinafter) obtained through a reaction with SD include phenyl sodium and naphthyl sodium, the organosodium compound is not limited thereto.

The organosodium compound is preferably obtained by reacting, in a reaction solvent, SD with an organic compound having an aromatic ring. A solvent known in the art can be used as the reaction solvent as long as the reaction of SD with an organic compound having an aromatic ring is not inhibited. Examples thereof include ether-based solvents, normal paraffin-based solvents, cycloparaffin-based solvents, aromatic solvents, amine-based solvents, and heterocyclic compound-based solvents, and these solvents have been described above in detail. Preferably, the organosodium compound can be prepared by dripping an organic compound having an aromatic ring into a reaction solvent to which SD has been added, and then Na-TMPs can be synthesized by adding TMPs thereto.

In the method for synthesizing Na-TMPs according to this embodiment, in the reaction of TMPs with SD or an organosodium compound, an electron acceptor is added to the reaction system as needed. Any substance can be used as the electron acceptor as long as it can accept electrons from SD or the organosodium compound. Although examples of the electron acceptor include branched unsaturated hydrocarbons such as isoprene, linear unsaturated hydrocarbons such as 1,3-butadiene, aromatic hydrocarbons such as biphenyl, 4,4'-Di-tert-butylbiphenyl, and styrene, and polycyclic aromatic hydrocarbons such as naphthalene, phenanthrene, and anthracene, the electron acceptor is not limited thereto. There is no particular limitation on the time when the electron acceptor is added as long as the electron acceptor can accept electrons from SD or the organosodium compound. Preferably, a configuration may be adopted in which the electron acceptor is reacted therewith simultaneously with the reaction of TMPs with SD or the organosodium compound, or TMPs is reacted therewith after the electron acceptor has been reacted with SD or the organosodium compound. Note that Na-TMPs can be efficiently obtained in the reaction of TMPs with the organosodium compound without adding the electron acceptor.

Hereinafter, reaction conditions and a mechanism of a reaction of the method for synthesizing Na-TMPs according to this embodiment will be described in detail.

There is no particular limitation on the reaction temperature, and the reaction temperature can be set as appropriate depending on the types and amounts of TMPs, SD or the organosodium compound, and the reaction solvent, the reaction pressure, and the like. Specifically, it is preferable to set the reaction temperature to a temperature lower than the boiling point of the reaction solvent. Under increased pressure, the boiling point is higher than that under atmospheric pressure, and the reaction temperature can thus be set to a higher temperature. If a normal paraffin-based or cycloparaffin-based solvent is used, the reaction can also be performed at room temperature, and the reaction temperature is preferably 10 to 100° C., particularly preferably 20 to 80° C., and even more preferably room temperature to 50° C. Although it is not necessary to provide a particular temperature controlling means for heating, cooling, and the like, a temperature controlling means may be provided as needed. If an ether-based solvent, an aromatic solvent, an amine-based solvent, or a heterocyclic compound-based solvent is used in the reaction, Na-TMP produced in the synthesis undergoes a reaction with the solvent at room temperature, and thus the reaction temperature needs to be set to 0° C. or less.

There is also no particular limitation on the reaction time, and it is sufficient that the reaction time is set as appropriate depending on the types and amounts of the starting material, SD or the organosodium compound, and the reaction solvent, the reaction pressure, the reaction temperature, and the like. In general, the reaction time is 30 minutes or longer, preferably 30 minutes to 24 hours, and the reaction is particularly preferably performed for 1 to 12 hours. If THF or toluene is used as the reaction solvent, the reaction solvent needs to be used as soon as possible after it is prepared.

Also, the agents required in the method for synthesizing Na-TMPs according to this embodiment, namely TMPs, SD, the reaction solvent, and the like, can be handled stably in an atmosphere, thus making it possible to perform the reaction under normal pressure conditions in an atmosphere. However, because agents are highly reactive and generate heat, it is desired to perform the reaction in an inert gas atmosphere that is filled with argon gas, nitrogen gas, or the like. Also, an organosodium compound is unstable in an atmosphere, and thus it is necessary to perform the reaction in an inert gas atmosphere. Furthermore, if SD that has passed for a long period after it is prepared is used or air is mixed in, the yield decreases, and thus it is desired to remove as much moisture as possible from agents and a solvent.

The usage amount of SD or the organosodium compound can be set as appropriate depending on the types and amounts of TMPs and the reaction solvent. When TMPs are reacted with SD or the organosodium compound, it is preferable that 1.0 to 2.0 molar equivalents of the reaction solvent is used with respect to 1 mmol of the substance amount of the TMPs, and the TMPs are reacted with 2.1 to 2.5 molar equivalents of SD and 0.8 to 1.0 molar equivalent of the organochlorine compound or 1.0 to 1.2 molar equivalents of the organosodium compound in the reaction solvent. The substance amount of SD herein means the substance amount in terms of the alkali metal contained in SD. Also, if an electron acceptor is added, it is preferable to add, to the reaction system, 1.0 to 1.5 molar equivalents of the electron acceptor, 1.0 to 1.5 molar equivalents of SD, and 0.8 to 1.5 molar equivalents of TMEDA with respect to the TMPs.

Na-TMPs obtained using the method for synthesizing Na-TMPs according to this embodiment may be purified using a purification means known in the art, such as column chromatography, distillation, recrystallization, or the like. Also, a configuration may be adopted in which TMPs that have not reacted and have remained are collected, and are used in the method for synthesizing Na-TMPs again.

Although one example of the mechanism of a reaction in the method for synthesizing Na-TMPs according to this embodiment is shown in FIG. 1, the mechanism of the reaction is not limited thereto. The mechanism of the reaction in which Na-TMP is synthesized by reacting TMP with SD in the presence of isoprene, which is an electron acceptor, is illustrated in FIG. 1. The reaction of isoprene with SD releases electrons from sodium metal in SD. The electrons released from the sodium metal are transferred to isoprene to form an isoprene radical anion-sodium salt. It is conceivable that this isoprene radical anion-sodium salt then removes a proton from a nitrogen atom of TMP, and substitutes it for sodium to obtain Na-TMP.

In this manner, with the method for synthesizing Na-TMPs according to this embodiment, as a result of adding SD or an organosodium compound using TMPs as starting materials, and an electron acceptor as needed, the synthesis proceeds and Na-TMPs can be stably and efficiently synthesized. In general, if only sodium metal or the like is introduced into the reaction system, for example, local heat generation or the like causes unevenness in a temperature distribution in the reaction system, and it is difficult to stabilize the reaction conditions, resulting in disadvantages such as the occurrence of undesirable side reactions. On the other hand, SD used in the method for synthesizing Na-TMPs according to this embodiment uniformly disperses throughout the reaction system, and thus Na-TMP can be stably synthesized in a uniform temperature distribution.

In the method for synthesizing Na-TMPs according to this embodiment, SD, which is easy to handle, is used, and thus Na-TMPs can be manufactured through a small number of steps under mild conditions in a simple manner in a short period of time without requiring a complicated chemical technique, and thus this method is economically and industrially very advantageous.

Because TMPs are bulky and electron-rich, anions formed due to protons of nitrogen of TMPs being removed are unstable. Thus, it is difficult to produce sodium amide of TMPs, but in the method for synthesizing Na-TMPs according to this embodiment, as a result of using SD, this synthetic reaction system can stably proceed, and Na-TMPs can be stably and efficiently synthesized. Also, if an organosodium compound is used, there is an advantage that expensive N,N,N',N'-tetramethylethylenediamine (which may be abbreviated as "TMEDA" hereinafter) is not used and no byproducts derived from isoprene are produced.

The obtained Na-TMPs can be directly used or subjected to functional group modification or the like to synthesize pharmaceuticals, animal drugs, and agricultural chemicals etc.

(Method for Synthesizing Na-TMPs According to Another Embodiment of Present Invention)

In a method for synthesizing Na-TMPs according to another embodiment, amines can be added, as an additive, to the reaction system of TMPs and SD or an organosodium compound.

Any of aliphatic amines, aromatic amines, and heterocyclic amines can be used as the amines, and the amines may have any of a primary amino group, a secondary amino group, or a tertiary amino group, and may have one or more amino groups. N,N,N',N'-tetramethylethylenediamine, N,N,N',N'',N''-pentamethyldiethylenetriamine, ethylamine, ethylenediamine, diethylamine, triethylamine, diethylenetriamine, diisopropylethylamine, N,N,N',N'-tetraethylethylenediamine (which may be abbreviated as "TEEDA" hereinafter), N,N,N',N'-tetramethyl-1,3-propanediamine, pyridine, pyrrolidine, N-methylpiperidine, N-methylpyrrolidine, and the like can be used as the amines, and TMEDA is particularly preferable. These amines may be used alone or in combination of two or more.

There is no particular limitation on the time when amines are added, and amines may be added simultaneously with the time when the reaction of TMPs with SD or an organosodium compound is started, or before or after the reaction is started.

As a result of adding amines, the reaction system for synthesizing Na-TMPs is stabilized and the progress of the reaction can be facilitated, and Na-TMPs can be more stably and efficiently synthesized. Reasons for this are that Na-TMPs, which are the products, are ionic compounds, and thus are unstable in a nonpolar solvent such as hexane that is suitably used as the reaction solvent. Thus, Na-TMPs are present in a nonpolar solvent in a state in which most of the Na+ cations are exposed. If a Lewis base, which is a donor for a lone electron pair of amines or the like, is coordinated here, Na-TMP form complexes with amines, the solubility of the Na-TMPs in the nonpolar solvent is increased and the system in which the Na-TMPs are produced is stabilized. It is conceivable that stabilization of the production system increases the frequency of collision between TMPs and SD or an organosodium compound, and stabilization of a transition state increases the force for driving the reaction for synthesizing Na-TMPs, and the progress of the synthetic reaction is facilitated and the yield is increased.

Also, as described above, because TMPs are bulky and electron-rich, anions formed due to protons of nitrogen of TMPs being removed are unstable. Thus, it is difficult to produce sodium amides of TMPs, but as a result of using amines in addition to SD, this synthetic reaction system can stably proceed and Na-TMPs can be stably and efficiently synthesized.

Na-TMPs synthesized using the method for synthesizing Na-TMPs according to this embodiment can be used as bases in various reactions, and can be used in organic synthesis of pharmaceuticals, animal drugs, agricultural chemicals, and the like.

(Method for Evaluating Production of Na-TMPs of Present Invention)

The production of Na-TMPs synthesized using the method for synthesizing Na-TMPs according to the above-described embodiment can be evaluated by reacting a product with fluorene, quenching the reaction using heavy water, and measuring the quenched product using 1H-NMR. If Na-TMPs are present, one of two hydrogen atoms of a carbon atom located at 9-position of fluorene is removed and substituted by sodium from Na-TMP. Then, fluorene is deuterated through quenching with heavy water. The yield of Na-TMPs, which are products, can be analyzed from the amount of deuterated fluorene.

Because Na-TMPs have a dark brown color, production of Na-TMPs cannot be evaluated accurately using a colorimetric titration method (e.g., see M. E. Brown et. al., J. Org. Chem., 2002, 67(25), p 9087-9088) in which 9-methylfluorene etc. that is known as an indicator in the titration of Group IA and Group IIA organometallic reagents. In the method for evaluating production of Na-TMPs according to this embodiment, production of Na-TMPs can be accurately evaluated by deprotonating fluorene and quenching the reaction with heavy water.

EXAMPLES

Hereinafter, the present invention will be described in detail by use of examples, but the present invention is not limited to these examples. In these examples, synthesis of Na-TMP that does not have a substituent was investigated. A dispersion product obtained by dispersing minute particles of sodium metal in normal paraffin oil was used as SD, and the amount of SD was a value in terms of sodium metal contained in SD.

Example 1. Investigation of Synthesis Conditions in Method for Synthesizing Na-TMP Using SD In this example, with regard to the synthesis of Na-TMP using SD, reaction conditions such as reaction solvents, additives, and reaction times were investigated (see FIG. 2). Note that the equivalent refers to a molar equivalent with respect to TMP introduced into the reaction system. Also, here, a yield is obtained by dividing the amount of Na-TMP that was actually acquired by the amount of added SD and showing the obtained ratio as a percentage.

Experiment Number 1

In 1 M cyclohexane (a reaction solvent), 1.1 equivalents of TMP was dissolved, and 1 equivalent of SD and 1.1 equivalents of isoprene were added thereto and reacted therewith at 25° C. for 12 hours. After the reaction, 1.1 equivalents of fluorene was added to the product and reacted therewith at 25° C. for 30 minutes, the reaction was quenched with heavy water, the obtained deuterated fluorene was analyzed by 1H-NMR, and thus the product was evaluated and the yield was calculated. The yield of Na-TMP was 45%.

Experiment Number 2

A reaction was performed in the same manner as in Experiment Number 1, except that 2 M cyclohexane was used as a reaction solvent, instead of 1 M cyclohexane, and was reacted therewith for 30 hours, and the yield was calculated. Specifically, in 2 M cyclohexane (the reaction solvent), TMP was dissolved, and 1 equivalent of SD and 1.1 equivalents of isoprene were added thereto and reacted therewith at 25° C. for 30 hours. The yield of Na-TMP was 77%.

Experiment Number 3

A reaction was performed in the same manner as in Experiment Number 1, except that hexane was used as a reaction solvent, instead of cyclohexane, and the yield was calculated. Specifically, in 1 M hexane (the reaction solvent), TMP was dissolved, and 1 equivalent of SD and 1.1 equivalents of isoprene were added thereto and reacted therewith at 25° C. for 12 hours. The yield of Na-TMP was 62%.

Experiment Number 4

A reaction was performed in the same manner as in Experiment Number 3, except that 1 equivalent of N,N,N', N'-tetramethylethylenediamine (referred to as "TMEDA" hereinafter) was added thereto as an additive and was reacted therewith for 0.5 hours, and the yield was calculated. Specifically, in 1 M hexane (the reaction solvent), TMP was dissolved, and 1 equivalent of SD, 1.1 equivalents of isoprene, and 1.1 equivalents of TMEDA were added thereto and reacted therewith at 25° C. for 0.5 hours. The yield of Na-TMP was 79%.

Experiment Number 5

A reaction was performed in the same manner as in Experiment Number 4, except that the reaction time was set to 1 hour, and the yield was calculated. Specifically, in 1 M hexane (the reaction solvent), TMP was dissolved, and 1 equivalent of SD, 1.1 equivalents of isoprene, and 1 equivalent of TMEDA were added thereto and reacted therewith at 25° C. for 1 hour. The yield of Na-TMP was 88%.

Experiment Number 6

A reaction was performed in the same manner as in Experiment Number 4, except that the reaction time was set to 12 hours, and the yield was calculated. Specifically, in 1 M hexane (the reaction solvent), TMP was dissolved, and 1 equivalent of SD, 1.1 equivalents of isoprene, and 1 equivalent of TMEDA were added thereto and reacted therewith at 25° C. for 12 hours. The yield of Na-TMP was 89%.

Experiment Number 7

A reaction was performed in the same manner as in Experiment Number 3, except that 1 equivalent of N,N,N', N'',N''-pentamethyldiethylenetriamine was added as an additive and reacted therewith for 1 hour, and the yield was calculated. Specifically, in 1 M hexane (the reaction solvent), TMP was dissolved, and 1 equivalent of SD, 1.1 equivalents of isoprene, and 1 equivalent of N,N,N',N'',N''-pentamethyldiethylenetriamine were added thereto and reacted therewith at 25° C. for 1 hour. The yield of Na-TMP was 60%.

Experiment Number 8

A reaction was performed in the same manner as in Experiment Number 3, except that 1 equivalent of 1,2- dimethoxyethane (referred to as "DME" hereinafter) was added as an additive, and the yield was calculated. Specifically, in 1 M hexane (the reaction solvent), TMP was dissolved, and 1 equivalent of SD, 1.1 equivalents of isoprene, and 1 equivalent of DME were added thereto and reacted therewith at 25° C. for 12 hours. Only trace amounts of Na-TMP were obtained.

Figure 2:
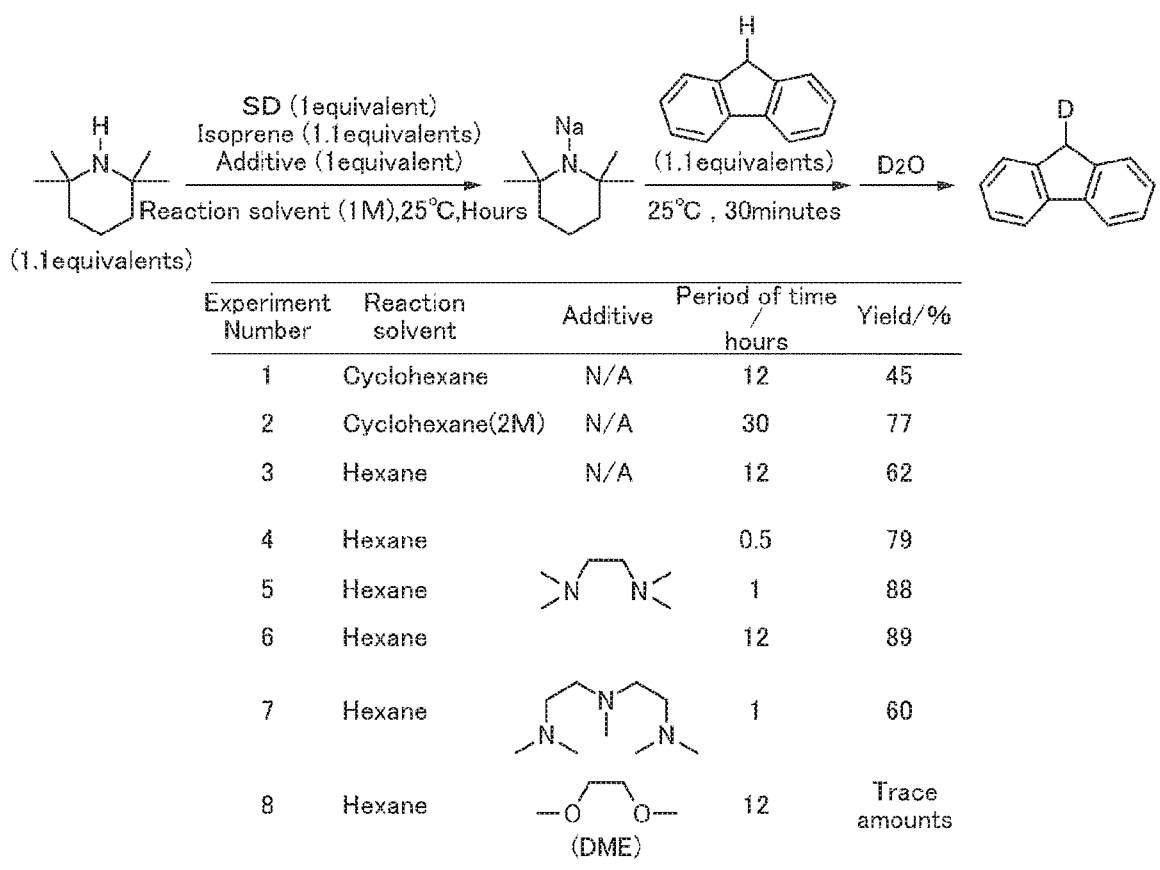
FIG. 2 is a diagram summarizing the investigation conditions and the investigation results of Example 1 in which a method for synthesizing Na-TMPs using SD according to this embodiment was investigated.

A reaction scheme, reaction conditions, and yields are summarized in FIG. 2. It is confirmed that, if no additive is added or TMEDA and N,N,N',N'',N''-pentamethyldiethylenetriamine, which are amines, are added as additives, Na-TMP can be synthesized under mild conditions. In particular, if hexane is used as a reaction solvent and TMEDA, which is an amine, are added as an additive, the synthetic reaction acceleration effect was confirmed, and it was found that Na-TMP can be synthesized at a high yield (about 90%) even in a short reaction time. It was found that even if N,N,N',N'',N''-pentamethyldiethylenetriamine is added, Na-TMP can be synthesized at a high yield in one-hour short reaction time.

Example 2. Investigation of Synthesis Conditions in Method for Synthesizing Na-TMP Using Organosodium Compound Having Aromatic Ring Obtained Through Reaction with SD-1

Figure 3:
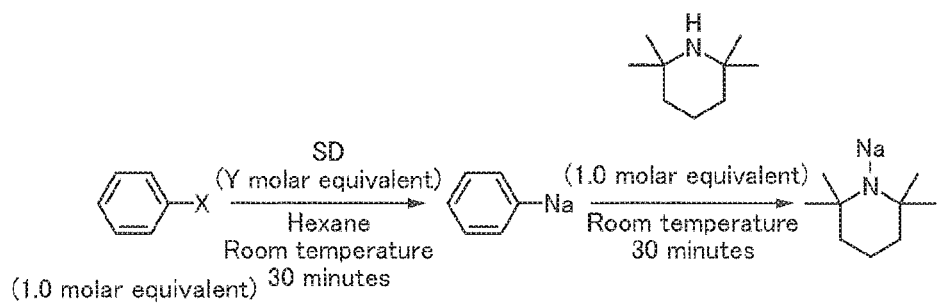
FIG. 3 is a diagram summarizing the investigation conditions and the investigation results of Example 2 in which a method for synthesizing Na-TMPs using an organosodium compound having an aromatic ring obtained through a reaction with SD according to this embodiment was investigated.

In this example, with regard to the synthesis of Na-TMP using an organosodium compound having an aromatic ring obtained through a reaction with SD, reaction conditions such as reaction solvents, additives, and reaction times were investigated (see FIG. 3).

Experiment Numbers 1 to 9

In 0.5 ml of hexane, 0.5 mmol of halogenated benzene, which is a starting compound, and Y molar equivalent of SD were added thereto and reacted therewith at room temperature for 30 minutes to synthesize phenyl sodium, and 1.0 molar equivalent of TMP was reacted with the synthesized phenyl sodium at room temperature for 30 minutes, and the obtained Na-TMP was reacted with fluorene, the reaction was quenched with heavy water, and the quenched product was measured by 1H NMR. In Experiment Numbers 1 to 4, bromobenzene was used as a starting material, and 2.0, 2.1, 2.2, and 2.3 molar equivalents of SD were added to bromobenzene. In Experiment Numbers 5 to 9, chlorobenzene was used as a starting material, and 1.95, 2.0, 2.1, 2.2, and 2.3 molar equivalents of SD were added to chlorobenzene.

A ratio (%) of Na-TMP, which was actually obtained, to Na-TMP that can be theoretically produced from halogenated benzene added to the reaction system was calculated as the yield. Also, in order to evaluate whether or not a Wurtz reaction in which halogenated benzene molecules are coupled is induced, production of a coupling product (Ph-Ph) was measured by 1H NMR, and a Ph-Ph production ratio (%) was calculated.

A reaction scheme, reaction conditions, types of base, and yields are summarized in FIG. 3. As a result, it is understood that, if bromobenzene is used as a starting compound, when 2.2 molar equivalents or more of SD are reacted therewith, Na-TMP can be synthesized at a high yield of 99% or more. Also, it is understood that, if chlorobenzene is used as a starting compound, when 2.1 molar equivalents or more of SD are reacted therewith, Na-TMP can be synthesized at a high yield of 99% or more. On the other hand, it was found that, if the amount of SD is less than 2.0 molar equivalents, a Wurtz reaction, which is a side reaction, is induced, and the yield of Na-TMP is reduced.

Example 3. Investigation of Stability of Na-TMP

Figure 4:
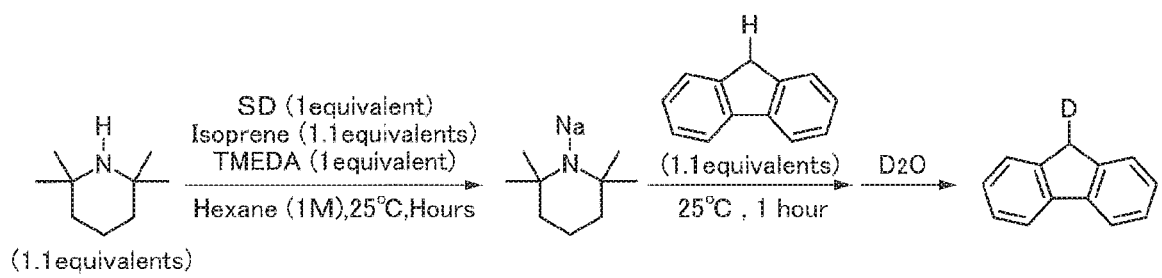
FIG. 4 is a diagram summarizing the investigation conditions and the investigation results of Example 3 in which the stability of a product synthesized using a method for synthesizing Na-TMPs using SD according to this embodiment was investigated.

In this example, the stability of Na-TMP synthesized using SD was investigated (see FIG. 4). Note that the equivalent refers to a molar equivalent. Also, here, a yield is obtained by dividing the amount of Na-TMP that was actually acquired by the amount of added SD and showing the obtained ratio as a percentage.

In 1 M hexane (the reaction solvent), 1.1 equivalents of TMP was dissolved, 1 equivalent of SD, 1.1 equivalents of isoprene, and 1 equivalent of TMEDA serving as an additive were added thereto and reacted therewith at 25° C. for 0.5, 1, 3, 6, 12, or 24 hours (Experiment Numbers 1 to 7). After the reaction, 1.1 equivalents of fluorene was added to the product and reacted therewith at 25° C. for 1 hour, the reaction was quenched with heavy water, the obtained deuterated fluorene was analyzed by 1H-NMR, and thus the product was evaluated and the yield was calculated. The yields of Na-TMP were 79% (0.5 hours), 88% (1 hour), 87% (3 hours), 86% (6 hours), 89% (12 hours), and 80% (24 hours).

A reaction scheme, reaction conditions, and yields are summarized in FIG. 4. It was confirmed that, even if the reaction time was longer, the yield of Na-TMP synthesized using SD was almost constant. Accordingly, it was found that Na-TMP maintained its activity and was stably present in the hexane solvent.

Figure 5:
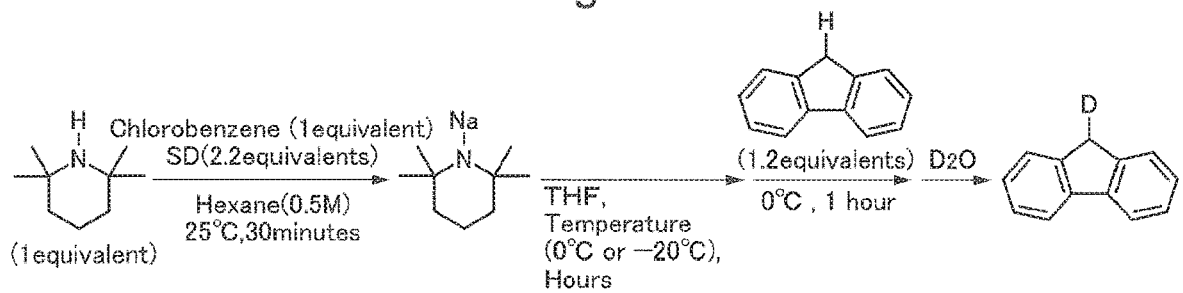
FIG. 5 is a diagram summarizing the investigation conditions and the investigation results of Example 3 in which the stability of products synthesized using a method for synthesizing Na-TMPs using an organosodium compound having an aromatic ring obtained through a reaction with SD according to this embodiment was investigated.

Also, the stability of Na-TMP when THF was added to Na-TMP synthesized using hexane as the reaction solvent and an organosodium compound having an aromatic ring obtained through a reaction with SD was investigated (see FIG. 5). Note that the equivalent refers to a molar equivalent. Also, here, a ratio (%) of Na-TMP, which was actually obtained, to Na-TMP that can be theoretically produced from TMP added to the reaction system was calculated as the yield.

In 0.5 M hexane (the reaction solvent), 2.2 equivalents of SD was added thereto, 1 equivalent of chlorobenzene was dripped to prepare phenyl sodium, and TMP was then added thereto and reacted at 25° C. for 30 minutes. After the reaction, THF was added to the product and stored at 0° C. (Experiment Numbers 1 to 7) or −20° C. (Experiment Numbers 8 to 14) for 0, 1, 3, 6, 12, 18, or 24 hours, 1.2 equivalents of fluorene was added thereto and reacted therewith at 0° C. for 1 hour, the reaction was quenched with heavy water, the obtained deuterated fluorene was analyzed by 1H-NMR, and thus the products were evaluated and the yields were calculated. The yields of Na-TMP were, in the experimental system in which products were stored at 0° C. (Experiment Numbers 1 to 7), 98% (0 hours), 91% (1 hour), 75% (3 hours), 63% (6 hours), 63% (12 hours), 44% (18%), and 38% (24 hours), and in the experimental system in which products were stored at −20° C. (Experiment Numbers 8 to 14), 98% (0 hours), 89% (1 hour), 90% (3 hours), 84% (6 hours), 73%(12 hours), 56%(18 hours), and 51% (24 hours). According to the results of experiments, it was found that Na-TMP was stable in the presence of THF at 0° C. for 1 hour, and at −20° C. for 3 hours.

Example 4. Investigation of Temporal Stability of SD

Figure 6:
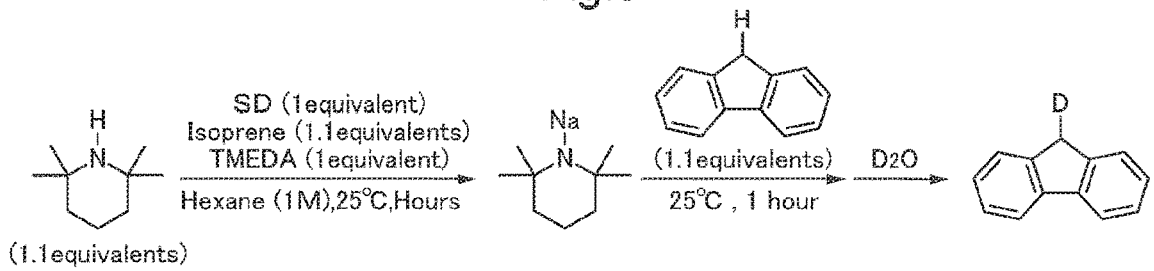
FIG. 6 is a diagram summarizing the investigation conditions and the investigation results of Example 4 in which the temporal stability of SD used in a method for synthesizing Na-TMPs using SD according to this embodiment was investigated.

In this example, a temporal change in the quality of SD was investigated (see FIG. 6). Note that the equivalent refers to a molar equivalent. Also, here, a yield is obtained by dividing the amount of Na-TMP that was actually acquired by the amount of added SD and showing the obtained ratio as a percentage.

Experiment Number 1

In 1 M hexane (the reaction solvent), 1.1 equivalents of TMP was dissolved, 1 equivalent of SD, 1.1 equivalents of isoprene, and 1 equivalent of TMEDA were added thereto and reacted therewith at 25° C. for 0.5 hours. Used SD had passed 4 days after its packaging material was opened. After the reaction, 1.1 equivalents of fluorene was added to the product and reacted therewith at 25° C. for 1 hour, the reaction was quenched with heavy water, the obtained deuterated fluorene was analyzed by 1H-NMR, and thus the product was evaluated and the yield was calculated. The yield of Na-TMP was 90%.

Experiment Numbers 2 to 7

TMPs, SD, isoprene, and TMEDA were reacted with each other in hexane for 1 hour in the same manner as in Experiment Number 1, and then the yield of Na-TMP was calculated. Used SDs had passed 6 days (Experiment Number 2), 8 days (Experiment Number 3), 10 days (Experiment Number 4), 13 days (Experiment Number 5), 30 days (Experiment Number 6), and 32 days (Experiment Number 7), after being opened. The yields of Na-TMP were 89% (Experiment Number 2), 88% (Experiment Number 3), 87% (Experiment Number 4), 82% (Experiment Number 5), 77% (Experiment Number 6), and 72% (Experiment Number 7).

A reaction scheme, reaction conditions, a period of time (age in days) elapsed after SD was opened, and yields are summarized in FIG. 6. Although the activity of SD decreased and reproducibility decreased over time after SD was opened, a significant decrease was not confirmed in an investigation period. In particular, it was found that SD maintained its activity and exhibited good reproducibility within 10 days after SD was opened.

Example 5. Reaction Using Na-TMP—1

Figure 7:
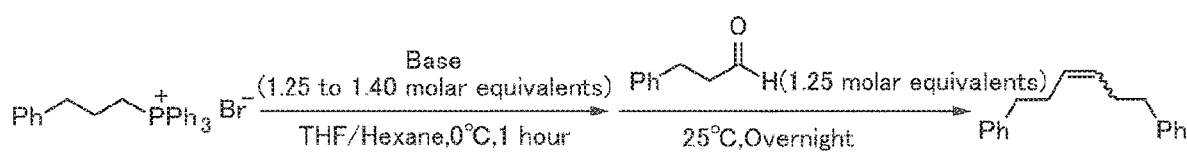
FIG. 7 is a diagram summarizing the investigation conditions and the investigation results of Example 5 in which reactions (a Wittig reaction) in which Na-TMP synthesized using a method for synthesizing Na-TMPs according to this embodiment was used were investigated.

In this example, a Wittig reaction in which Na-TMP was used was investigated (see FIG. 7). The Wittig reaction is a reaction in which an alkene is produced through a reaction of a Wittig reagent (phosphorus ylide) with an aldehyde (or ketone), and the Wittig reagent can be synthesized by treating, with a base, a phosphonium salt produced by reacting triphenylphosphine with an alkyl halide.

Experiment Numbers 1 to 3

In Experiment Numbers 1 to 3, 1.25 molar equivalents of Li-TMP (Experiment Number 1), 1.4 molar equivalents of Li-TMP/NaO$^t$Bu (Experiment Number 2), and 1.25 molar equivalents of Na-TMP (Experiment Number 3) were used as bases, and in THF/hexane, a phosphonium salt was reacted therewith at 0° C. for 1 hour, and then reacted with 1.25 molar equivalents of an aldehyde compound at 25° C. overnight to produce an alkene. After the reaction, the alkene, which was the product, was evaluated through analysis by 1H-NMR, and the yield was calculated. Also, the production ratio of cis-trans isomers of the produced alkene was evaluated through GC. The yields thereof in the case of using Li-TMP, Li-TMP/NaO$^t$Bu, and Na-TMP as bases were respectively 89%, 96%, and 92%. Also, cis-trans selectivities (E/Z) were respectively 18/82, 12/88, and 8/92.

A reaction scheme, reaction conditions, types of base, yields, and cis-trans selectivity are summarized in FIG. 7. As a result, it was confirmed that, as a result of using Na-TMP as a base, an alkene was produced at a yield equivalent to that in the case where a compound containing Li was used as a base. Also, it was found that, as a result of using Na-TMP, the production ratio of a cis(Z)-alkene was high, and good Z-selectivity was obtained.

Example 6. Reaction Using Na-TMP—2

Figure 8:
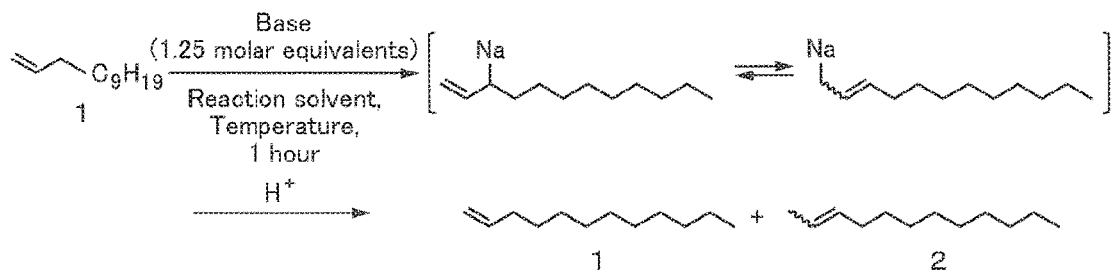
FIG. 8 is a diagram summarizing the investigation conditions and the investigation results of Example 6 in which reactions (an isomerization reaction via deprotonation of a hydrogen atom located at an allylic position) in which Na-TMP synthesized using a method for synthesizing Na-TMPs according to this embodiment was used were investigated.

In this example, an isomerization reaction via deprotonation of a hydrogen atom located in an allylic position using Na-TMP was investigated (see FIG. 8). Here, investigation was conducted using 1-dodecene having one double bond in the molecular chain.

Experiment Number 1

Deprotonation was performed by reacting, in a reaction solvent, 1-dodecene with Na-TMP serving as a base for a predetermined period of time, and then protons were added thereto. Specifically, in a hexane solvent, 1.25 molar equivalents of Na-TMP was reacted with 1-dodecene at 0° C. for 1 hour, and then protons were added thereto. After the reaction, 1-dodecene 1 or 2-dodecene 2, which was the product, was evaluated through analysis by 1H-NMR, and the yields were calculated. Also, the production ratio of cis-trans isomers of 2-dodecene 2 was evaluated through GC. The yields of 1-dodecene 1 and 2-dodecene 2 (cis-trans selectivity) were respectively 1% and 98% (E/Z=73/27).

Experiment Number 2

A reaction was performed in the same manner as in Experiment Number 1, except that THF:hexane=1:2 was used as a reaction solvent, and the yields and the cis-trans selectivity were calculated. The yields of 1-dodecene 1 and 2-dodecene 2 (cis-trans selectivity) were respectively 3% and 90% (E/Z=78/22).

Experiment Number 3

A reaction was performed in the same manner as in Experiment Number 1, except that the reaction temperature was set to 25° C., and the yields and the cis-trans selectivity were calculated. The yields of 1-dodecene 1 and 2-dodecene 2 (cis-trans selectivity) were respectively 2% and 91% (E/Z=62/38).

Experiment Number 4

A reaction was performed in the same manner as in Experiment Number 1, except that the amount of added Na-TMP was 10 mol % and Na-TMP was reacted therewith at a reaction temperature of 25° C. for 5 hours, and the yields and the cis-trans selectivity were calculated. The yields of 1-dodecene 1 and 2-dodecene 2 (cis-trans selectivity) were respectively 1% and 98% (E/Z=73/27).

Experiment Number 5

A reaction was performed in the same manner as in Experiment Number 1, except that Li-TMP was added instead of Na-TMP and was reacted therewith in THF at a reaction temperature of 25° C., and the yields and the cis-trans selectivity were calculated. The yields of 1-dodecene 1 and 2-dodecene 2 (cis-trans selectivity) were respectively 95% and 4% (E/Z=45/55).

Experiment Number 6

A reaction was performed in the same manner as in Experiment Number 1, except that Li-TMP was added in the same manner as in Experiment Number 5, instead of Na-TMP, and was reacted therewith in THF at a reaction temperature of 50° C., and the yields and the cis-trans selectivity were calculated. The yields of 1-dodecene 1 and 2-dodecene 2 (cis-trans selectivity) were respectively 59% and 39% (E/Z=47/53).

A reaction scheme, reaction conditions, types of base, yields, and cis-trans selectivity are summarized in FIG. 8. It was confirmed that, if Na-TMP was used as a base, protons with low acidity were removed through deprotonation of a hydrogen atom located at an allylic position. On the other hand, if Li-TMP was used as a base, protons with low acidity were unlikely to be removed under reaction conditions at 25° C., and the production ratio of 2-dodecene was very low. The production ratio of 2-dodecene was also very low under reaction conditions at 50° C., compared to the case where Na-TMP was used.

Example 7. Reaction Using Na-TMP—3

In this example, deprotonation and a functionalization reaction of a heteroarene using Na-TMP were investigated (see FIG. 9). Here, investigation was conducted using dibenzofuran, which is a heterocyclic compound, as a heteroarene.

Experiment Number 1

Deprotonation was performed by reacting, in a hexane solvent, dibenzofuran with "BuLi serving as a base for a predetermined period of time. Specifically, in a hexane solvent, 1.1 molar equivalents of Na-TMP was reacted with 0.45 moles of benzofuran at 25° C. for 30 minutes, the reaction was then quenched with heavy water, the obtained deuterated dibenzofuran was analyzed by 1H-NMR, and thus the product was evaluated and the yield was calculated. The yield was 79%.

Experiment Number 2

A reaction was performed in the same manner as in Experiment Number 1, except that THF:hexane=1:2 was used as a reaction solvent and reacted at 0° C., and the yield was calculated. The yield was 85%.

Experiment Number 3

A reaction was performed in the same manner as in Experiment Number 1, except that Li-TMP was added instead of "BuLi, and the yield was calculated. The yield was 14%.

Experiment Number 4

A reaction was performed in the same manner as in Experiment Number 1, except that Li-TMP was added in the same manner as in Experiment Number 3, instead of "BuLi, and THF:hexane=1:2 was used as a reaction solvent and reacted at 0° C., and the yield was calculated. The yield was 50%.

Experiment Number 5

A reaction was performed in the same manner as in Experiment Number 1, except that Na-TMP was added instead of "BuLi, and the yield was calculated. The yield was 90%.

A reaction scheme, reaction conditions, types of base, and yields are summarized in FIG. 9. It was confirmed that, as a result of using Na-TMP as a base, a heteroarene was efficiently deprotonated. It was also confirmed, through a comparison with the case where "BuLi and Li-TMP were used, that the efficiency of deprotonation was high.

It was also found that, if an electrophilic agent was reacted therewith, a heteroarene substitution reaction efficiently proceeded. For example, 1-bromodibenzofuran was produced at a yield of 84% through a reaction with tetrabromoethane that is an electrophilic agent. Also, 1-benzoyldibenzofuran was produced at a yield of 72% through a reaction with benzoyl chloride that is an electrophilic agent. Also, dibenzofuran substituted by an allyl group was produced through a reaction with allyl bromide that is an electrophilic agent, and specifically, 1-(2-propenyl)-dibenzofuran was produced at a yield of 37% through a reaction with 1-bromopropene. It was found that, as a result of optimizing reaction conditions, a further improvement in the yield was expected, and Na-TMP can be used in various substitution reactions.

Example 8. Reaction Using Na-TMP—4

In this example, a functionalization reaction of a heterocyclic compound using Na-TMP was investigated (see FIG. 10).

Experiment Number 1

In a 0.5 M hexane solvent, 1.25 molar equivalents of Na-TMP was reacted with 0.4 mmol of benzo[b]thiophene (arene) at room temperature for 1 hour, and then 1.5 molar equivalents of boric acid ester (trimethyl borate $(B(OMe)_3)$: an electrophilic reagent) was reacted therewith in a 0.2 M hexane solvent at 0° C. for 1 hour. Then, hydrochloric acid was added and reacted therewith at room temperature for 2 hours. The product was evaluated through analysis by 1H-NMR, and the yield of isolated benzo[b]thiophene-2-boronic acid in which a boronyl group ($—B(OH)_2$) was added to 2-position of benzo[b]thiophene was calculated. The isolated yield is a value obtained by dividing the amount of product by a difference between the amount of a starting raw material and the amount of the raw material collected after the reaction (the net used amount). The isolated yield was 64%.

Experiment Number 2

In 0.5 M hexane solvent, 1.25 molar equivalents of Na-TMP was reacted with 0.4 mmol of benzo[b]thiophene (arene) at 25° C. for 30 minutes, 1.5 molar equivalents of heavy water ($D_2O$: electrophilic reagent) was then added thereto and reacted therewith at 0° C. for 1 hour. The product was evaluated through analysis by 1H-NMR, and the yield of isolated deuterated benzo[b]thiophene in which a hydrogen atom located at 2-position of benzo[b]thiophene was substituted by heavy hydrogen was calculated in the same manner as in Experiment Number 1. The isolated yield was 99%.

Experiment Number 3

A reaction was performed using benzo[b]thiophene as an arene and iodomethane (MeI) as an electrophilic reagent in the same manner as in Experiment Number 2, the product was then evaluated, and the yield of isolated 2-methyl-benzo[b]thiophene in which a methyl group (-Me) was added at 2-position of benzo[b]thiophene was calculated. The isolated yield was 77%.

Experiment Number 4

A reaction was performed using benzo[b]thiophene as an arene and an allyl bromide (allylBr) as an electrophilic reagent in the same manner as in Experiment Number 2, the product was then evaluated, and the yield of isolated 2-allyl-benzo[b]thiophene in which an allyl group was added at 2-position of benzo[b]thiophene was calculated. The isolated yield was 82%.

Experiment Number 5

A reaction was performed using benzo[b]thiophene as an arene and a benzoyl chloride (PhC(O)Cl) as an electrophilic reagent in the same manner as in Experiment Number 2, the product was then evaluated, and the yield of isolated 2-benzoyl-benzo[b]thiophene in which a benzoyl group was added at 2-position of benzo[b]thiophene was calculated. The isolated yield was 66%.

Experiment Number 6

A reaction was performed using benzo[b]thiophene as an arene and carbon dioxide ($CO_2$) as an electrophilic reagent in the same manner as in Experiment Number 2, the product was then evaluated, and the yield of isolated benzo[b]

thiophene-2-carboxylic acid in which a carboxy group (—CO$_2$H) was added at 2-position of benzo[b]thiophene was calculated. The isolated yield was 89%.

Experiment Number 7

Benzo[b]thiophene was used as an arene, and 1,1,2,2-tetrabromoethane (Br$_2$HCCHBr$_2$) was used as an electrophilic reagent. The arene was reacted with Na-TMP in the same manner as in Experiment Number 2, the electrophilic reagent was added thereto and reacted therewith at −78° C. for 1 hour, the product was then evaluated, and the yield of isolated 2-bromo-benzo[b]thiophene in which a bromo group (—Br) was added at 2-position of benzo[b]thiophene was calculated. The isolated yield was 81%.

Experiment Number 8

Benzo[b]thiophene was used as an arene, and hexachloroethane (Cl$_3$CCCl$_3$) was used as an electrophilic reagent. The arene was reacted with Na-TMP in the same manner as in Experiment Number 2, the electrophilic reagent was added thereto and reacted therewith at −78° C. for 1 hour, the product was then evaluated, and the yield of isolated 2-chloro-benzo[b]thiophene in which a chloro group (—Cl) was added at 2-position of benzo[b]thiophene was calculated. The isolated yield was 91%.

Experiment Number 9

A reaction was performed using benzo[b]thiophene as an arene and a chlorotrimethylsilane (Me$_3$SiCl) as an electrophilic reagent in the same manner as in Experiment Number 2, the product was then evaluated, and the yield of isolated 2-trimethylsilyl-benzo[b]thiophene in which a trimethylsilyl group (—SiMe$_3$) was added at 2-position of benzo[b]thiophene was calculated. The isolated yield was 98%.

Experiment Number 10

A reaction was performed using benzo[b]thiophene as an arene and a chlorodiphenylphosphine (Ph$_2$PCl) as an electrophilic reagent in the same manner as in Experiment Number 2, the product was then evaluated, and the yield of isolated 2-diphenylphosphino-benzo[b]thiophene in which a diphenylphosphino group (—PPh$_2$) was added at 2-position of benzo[b]thiophene was calculated. The isolated yield was 72%.

Example 11

A reaction was performed using benzo[b]furan as an arene and a chlorotrimethylsilane (Me$_3$SiCl) as an electrophilic reagent in the same manner as in Experiment Number 2, the product was then evaluated, and the yield of isolated 2-trimethylsilyl-benzo[b]furan in which a trimethylsilyl group (—SiMe$_3$) was added at 2-position of benzo[b]furan was calculated. The isolated yield was 82%.

Example 12

A reaction was performed using dibenzofuran as an arene and a chlorotrimethylsilane (Me$_3$SiCl) as an electrophilic reagent in the same manner as in Experiment Number 2, the product was then evaluated, and the yield of isolated 4-trimethylsilyl-dibenzofuran in which a trimethylsilyl group (—SiMe$_3$) was added at 4-position of dibenzofuran was calculated. The isolated yield was 83%.

Example 13

A reaction was performed using dibenzofuran as an arene and a benzoyl chloride (PhC(O)Cl) as an electrophilic reagent in the same manner as in Experiment Number 2, the product was then evaluated, and the yield of isolated 4-benzoyl-dibenzofuran in which a benzoyl group was added at 4-position of dibenzofuran was calculated. The isolated yield was 73%.

A reaction scheme, reaction conditions, and isolated yields are summarized in FIG. 10. It was confirmed that, as a result of using Na-TMP as a base, a substituent can be added to a heterocyclic compound, such as boronic acid being able to be synthesized from benzothiophene. There are advantages that, as a result of using Na-TMP in this manner, a substituent can be added to a heterocyclic compound under mild conditions in a short period of time, and various compounds such as boronic acid can be synthesized.

INDUSTRIAL APPLICABILITY

The present invention can be applied to all the technical fields in which a method for synthesizing Na-TMPs and Na-TMPs obtained using this synthesis method are used, and particularly to organic synthesis of pharmaceuticals, animal drugs, agricultural chemicals, and the like.

The invention claimed is:

1. A method for synthesizing sodium 2,2,6,6-tetramethylpiperidides comprising
    a step of obtaining sodium 2,2,6,6-tetramethylpiperidides by reacting, without adding an electron acceptor, in a reaction solvent, 2,2,6,6-tetramethylpiperidines with an organosodium compound having an aromatic ring which is selected from the group consisting of phenyl sodium, naphthyl sodium, tolyl sodium, and mixtures thereof and obtained through a reaction with a dispersion product obtained by dispersing sodium in a dispersion solvent, wherein
    the organosodium compound, obtained by dispersing sodium in the dispersion solvent, is added in amount of 2.1 to 2.5 molar equivalents, with respect to the 2,2,6,6-tetramethylpiperidines,
    the dispersion solvent is selected from the group consisting of aromatic solvents, normal paraffin-based solvents, heterocyclic compound-based solvents, and mixtures solvents, and
    the reaction solvent is selected from the group consisting of ether-based solvents, normal paraffin-based solvents, cycloparaffin-based solvents, aromatic solvents, amine-based solvents, heterocyclic compound-based solvents, and mixtures thereof.

2. The method for synthesizing sodium 2,2,6,6-tetramethylpiperidides according to claim 1,
    wherein the step is carried out in the presence of amines.

3. A method for synthesizing sodium 2,2,6,6-tetramethylpiperidides comprising
    a step of obtaining sodium 2,2,6,6-tetramethylpiperidides by reacting, with adding N,N,N',N'-tetramethylethylenediamine, in a reaction solvent, 2,2,6,6-tetramethylpiperidines, an organosodium compound having an aromatic ring which is selected from the group consisting of phenyl sodium, naphthyl sodium, tolyl sodium, and mixtures thereof and obtained through a reaction with a dispersion product obtained by dispersing sodium in a dispersion solvent, and an electron acceptor, wherein
    the organosodium compound, obtained by dispersing sodium in the dispersion solvent, is added in amount of 1.0 to 1.5 molar equivalents, with respect to the 2,2,6,6-tetramethylpiperidines, the dispersion solvent is selected from the group consisting of aromatic solvents, normal paraffin-based solvents, heterocyclic compound-based solvents, and mixtures thereof, and the reaction solvent is selected from the group consisting of ether-based solvents, normal paraffin-based solvents, cycloparaffin-based solvents, aromatic solvents, amine-based solvents, heterocyclic compound-based solvents, and mixtures thereof.

* * * * *